(12) United States Patent
Wen et al.

(10) Patent No.: US 7,529,336 B2
(45) Date of Patent: May 5, 2009

(54) SYSTEM AND METHOD FOR LAMINOGRAPHY INSPECTION

(75) Inventors: Kuang Pu Wen, Hsinchu (TW); Shih-Liang Chen, Taipei (TW); Meng Kun Lee, Sanchong (TW)

(73) Assignee: Test Research, Inc., Taipei (TW)

( * ) Notice: Subject to any disclaimer, the term of this patent is extended or adjusted under 35 U.S.C. 154(b) by 0 days.

(21) Appl. No.: 11/756,503

(22) Filed: May 31, 2007

(65) Prior Publication Data

US 2008/0298538 A1    Dec. 4, 2008

(51) Int. Cl.
    *G01N 23/00* (2006.01)
(52) U.S. Cl. .................................... 378/26; 378/41
(58) Field of Classification Search ............. 378/21–27, 378/41
    See application file for complete search history.

(56) References Cited

U.S. PATENT DOCUMENTS

| | | | |
|---|---|---|---|
| 4,926,452 A | 5/1990 | Baker et al. |
| 5,027,418 A | 6/1991 | Ikegaya et al. |
| 5,060,246 A | 10/1991 | Van Der Brug et al. |
| 5,081,656 A | 1/1992 | Baker et al. |
| 5,097,492 A | 3/1992 | Baker et al. |
| 5,113,425 A | 5/1992 | Zweig |
| 5,164,994 A | 11/1992 | Bushroe |
| 5,182,775 A | 1/1993 | Matsui et al. |
| 5,199,054 A | 3/1993 | Adams et al. |
| 5,259,012 A | 11/1993 | Baker et al. |
| 5,289,520 A | 2/1994 | Pellegrino et al. |
| 5,291,535 A | 3/1994 | Baker et al. |
| 5,351,278 A | 9/1994 | Koshishiba et al. |
| 5,388,136 A | 2/1995 | Halliday et al. |
| 5,426,685 A | 6/1995 | Pellegrino et al. |
| 5,455,870 A | 10/1995 | Sepai et al. |
| 5,500,886 A | 3/1996 | Duff |
| 5,524,132 A | 6/1996 | Ranadive |
| 5,541,856 A | 7/1996 | Hammermeister |
| 5,561,696 A | 10/1996 | Adams et al. |
| 5,583,904 A | 12/1996 | Adams |
| 5,592,562 A | 1/1997 | Rooks |
| 5,594,768 A | 1/1997 | Fujii et al. |
| 5,594,770 A | 1/1997 | Bowles et al. |
| 5,609,152 A | 3/1997 | Pellegrino et al. |
| 5,621,811 A | 4/1997 | Roder et al. |
| 5,631,738 A | 5/1997 | Childers |
| 5,659,483 A | 8/1997 | Rhodes et al. |

(Continued)

OTHER PUBLICATIONS

Kang, S.T., et al., A projection method for reconstructing x-ray images of arbitrary cross-section. NDT&E International 32:9-20 (1999).

*Primary Examiner*—Jurie Yun
(74) *Attorney, Agent, or Firm*—Baker & McKenzie LLP

(57) ABSTRACT

A laminography inspection system comprises an irradiation source, a plurality of linear image detectors defining an image plane, a fixed table for placement of a test object in a stationary position between the irradiation source and the image detectors, and a computing device for processing a plurality of images of the test object acquired from the image detectors. The irradiation source and the image detectors perform a plurality of parallel linear scanning passes across the area of the test object to acquire images of the test object under different viewing angles. Based on the acquired image data, the computing device determines a warp compensation and generates a cross-sectional image of a selected section within the test object.

14 Claims, 11 Drawing Sheets

U.S. PATENT DOCUMENTS

| | | | |
|---|---|---|---|
| 5,687,209 A | 11/1997 | Adams | |
| 5,719,952 A | 2/1998 | Rooks | |
| 5,751,784 A | 5/1998 | Enck | |
| 5,761,337 A | 6/1998 | Nishimura et al. | |
| 6,002,739 A | 12/1999 | Heumann | |
| 6,002,790 A | 12/1999 | Horvath et al. | |
| 6,076,411 A | 6/2000 | Horvath | |
| 6,084,663 A | 7/2000 | Seng | |
| 6,201,850 B1 | 3/2001 | Heumann | |
| 6,222,903 B1 | 4/2001 | Kim et al. | |
| 6,236,709 B1 | 5/2001 | Perry et al. | |
| 6,269,326 B1 | 7/2001 | Lejeune | |
| 6,314,201 B1 | 11/2001 | Roder | |
| 6,324,249 B1 | 11/2001 | Fazzio | |
| 6,327,333 B1 | 12/2001 | Uchida et al. | |
| 6,373,917 B1 | 4/2002 | Roder | |
| 6,445,767 B1 | 9/2002 | Karellas | |
| 6,463,121 B1 | 10/2002 | Milnes | |
| 6,480,564 B1 | 11/2002 | Kim et al. | |
| 6,483,890 B1 | 11/2002 | Malamud | |
| 6,485,176 B1 | 11/2002 | Chen et al. | |
| 6,490,368 B2 | 12/2002 | Roder | |
| 6,501,822 B2 | 12/2002 | Roder | |
| 6,563,905 B1 | 5/2003 | Primrose | |
| 6,570,954 B2 | 5/2003 | Rasche et al. | |
| 6,570,957 B2 | 5/2003 | Fuchs et al. | |
| 6,618,465 B2 | 9/2003 | Mohr et al. | |
| 6,628,745 B1 | 9/2003 | Annis et al. | |
| 6,628,746 B2 | 9/2003 | Eppler et al. | |
| 6,630,675 B2 | 10/2003 | Ghelmansarai | |
| 6,665,433 B2 | 12/2003 | Roder | |
| 6,671,349 B1 | 12/2003 | Griffith | |
| 6,707,877 B2 | 3/2004 | Bohn | |
| 6,717,415 B2 | 4/2004 | Sunter | |
| 6,738,450 B1 | 5/2004 | Barford | |
| 6,748,046 B2 | 6/2004 | Thayer | |
| 6,765,981 B2 | 7/2004 | Heumann | |
| 6,819,739 B2 | 11/2004 | Eppler | |
| 6,819,805 B2 | 11/2004 | Usikov | |
| 6,825,856 B1 | 11/2004 | Fazzio et al. | |
| 6,826,255 B2 | 11/2004 | Birdwell et al. | |
| 6,847,900 B2 | 1/2005 | Ragland | |
| 6,850,589 B2 | 2/2005 | Heumann et al. | |
| 6,853,744 B2 | 2/2005 | Mueller et al. | |
| 6,872,949 B2 | 3/2005 | Mizuoka et al. | |
| 6,885,724 B2 | 4/2005 | Li et al. | |
| 6,890,098 B2 | 5/2005 | Rosner et al. | |
| 6,895,072 B2 | 5/2005 | Schrock et al. | |
| 6,895,073 B2 | 5/2005 | Shih et al. | |
| 6,907,103 B2 | 6/2005 | Rosner et al. | |
| 6,907,110 B2 | 6/2005 | Apel et al. | |
| 6,928,185 B2 | 8/2005 | Yonezawa | |
| 6,965,662 B2 | 11/2005 | Eppler et al. | |
| 6,970,531 B2 | 11/2005 | Eberhard et al. | |
| 6,977,985 B2 | 12/2005 | Bohn et al. | |
| 6,980,627 B2 | 12/2005 | Qiu et al. | |
| 6,993,193 B2 | 1/2006 | Smith | |
| 7,010,086 B2 | 3/2006 | Chopra | |
| 7,099,432 B2 | 8/2006 | Ichihara et al. | |
| 7,099,435 B2 | 8/2006 | Heumann et al. | |
| 7,108,424 B2 | 9/2006 | Heumann et al. | |
| 7,110,490 B2 | 9/2006 | Eberhard et al. | |
| 7,123,688 B2 | 10/2006 | Negle | |
| 7,171,897 B2 | 2/2007 | Barajas et al. | |
| 7,177,389 B2 | 2/2007 | Gary | |
| 7,177,391 B2 | 2/2007 | Chapin et al. | |
| 7,231,013 B2 * | 6/2007 | Meyer | 378/58 |

\* cited by examiner

Reconstructed X-ray image for Z = 15 after application of shift factors $L_{sx}$ & $L_{sy}$ Reconstructed X-ray image for Z = 15 after application of shift factors $L_{sx}$, $L_{sy}$ and scale factor $f$ Reconstructed X-ray image for Z = -15 after application of shift factors $L_{sx}$ & $L_{sy}$ Reconstructed X-ray image for Z = -15 after application of shift factors $L_{sx}$, $L_{sy}$ and scale factor $f$

SYSTEM AND METHOD FOR LAMINOGRAPHY INSPECTION

FIELD OF THE INVENTION

The present invention generally relates to imaging techniques for industrial inspection, and more specifically to systems and methods for laminography inspection.

DESCRIPTION OF THE RELATED ART

X-ray laminography is a well-known imaging technique that generates cross-sectional images of selected planes within a test object for inspection. Conventionally, the X-ray laminography system includes an X-ray source, X-ray detectors defining an image plane, and a fixture base for placement of the test object to be scanned between the X-ray source and the detectors. To acquire X-ray images of the test object, the test object is usually scanned through a cycle of coordinated motion of either the X-ray source along with the detectors or the fixture base alone. During one scanning cycle, the configuration of the X-ray source, test object, and detectors is such that any point in a specific plane of the test object, also called "focal plane", is always projected to the same point in the image plane, while any point outside the focal plane is projected to a plurality of points in the image plane. As a result, the image of the focal plane will appear sharp while the images of other planes within the test object will experience movement with respect to the detectors, creating a blurred background upon which is superimposed the sharp image of the focal plane. Based on the images acquired by the detectors, a cross-sectional image of a selected section within the test object is reconstructed by a combination of the acquired images.

Numerous approaches have been explored to develop an effective laminography system, as described in U.S. Pat. No. 4,926,452 entitled "Automated Laminography System For Inspection of Electronics" issued to Baker et al.; U.S. Pat. No. 5,583,904 entitled "Continuous Linear Scan Laminography System And Method" issued to Adams; U.S. Pat. No. 6,324,249 entitled "Electronic Planar Laminography System and Method" issued to Fazzio; and U.S. Pat. No. 6,748,046 entitled "Off-center Tomosynthesis" issued to Thayer, all the disclosures of which are incorporated herein by reference.

One known approach implements a laminography system in which the X-ray source and detectors scan the fixed test object along a circular path to acquire images of the test object. Within one scanning cycle, a "stop-and-go" motion is performed to acquire images under different viewing angles at discrete points on the circular path. As a result, the scanning speed is relatively slow and the number of acquired images is limited. Moreover, the driving mechanism for a rotational scanning cycle is bulky and expensive and requires a complex manufacturing process.

Another known approach uses a single translational scan for acquiring images of the test object under different viewing angles. With this scanning scheme, the X-ray source has to be collimated to irradiate beam fans of X-rays that cover the entire width of the test object. In addition, an increased number of X-ray detectors is required so that the image data acquired with a single linear scanning pass are from a sufficient number of viewing angles. Though this laminography system performs a simple and fast scanning cycle, the greater amount of requisite detectors still contributes to an increase in the equipment cost. Moreover, the required collimation of the X-ray source adds complexity to the laminography system.

Other known approaches may also prescribe the use of a large format camera to acquire image data of the test object. During a scanning cycle, the test object is moved between the camera and the X-ray source at stationary positions so that different regions of the test object are simultaneously imaged under different viewing angles on the camera. Though this laminography system may save some driving mechanisms of the X-ray source and camera as they are stationary during each scanning cycle, the use of a large format camera is still costly. In addition, the motion of the test object during the scanning cycle may affect the quality of the image acquisition.

Another technical issue that may arise is the occurrence of a warp in the test object. A warp in the test object may result in a position of the section of interest that is actually biased relative to its assumed position. As a result, the laminographic cross-sectional image actually reconstructed may not represent the selected section plane, but another one offset from the desired section plane. To solve this problem, U.S. Pat. No. 5,678,209 describes a warp compensation mode of operation, the disclosure of which is incorporated herein by reference. This known warp compensation technique requires the use of predetermined computer-assisted design (CAD) data of the test object that are to be compared against captured image data of the test object to determine the warp of the test object. Based on the computed warp, the image shifts to be applied to reconstruct a cross-section image of the selected section then are determined. Practically, the application of this technique is inaccurate as the selected features often are not placed at the exact CAD position or the CAD data of the test objects are not available at all.

Therefore, there is a need for an improved laminography system that can overcome at least the foregoing problems of the prior art.

SUMMARY OF THE INVENTION

The present application describes a system and method for laminography inspection that can effectively generate a cross-sectional image of a selected section plane within a test object using a convenient warp compensation mode of computation.

In one embodiment, the laminography inspection system comprises an irradiation source, a plurality of linear image detectors defining an image plane, a fixed table for placement of a test object in a stationary position between the irradiation source and the image detectors, and a computing device for processing a plurality of images of the test object acquired from the image detectors. The irradiation source and the image detectors perform a scanning cycle comprised of parallel linear scanning passes spanning across the area of the test object. Images of the test object are thereby acquired under different viewing angles for processing by the computing device. The computing device combines the acquired images being adequately shifted and scaled to generate a cross-sectional image of a selected section within the test object.

According to some embodiments, the computing device may be configured to determine a warp compensation that is applied to the computation of the shift and scale factors for combining the acquired images of the test object. The warp compensation may be computed with a stereo imaging method.

One advantage of the system and method according to the present invention is that it is cost efficient, and allows for a convenient warp compensation mode of computation that does not require CAD data of the test object.

The foregoing is a summary and shall not be construed to limit the scope of the claims. The operations and structures disclosed herein may be implemented in a number of ways, and such changes and modifications may be made without departing from this invention and its broader aspects. Other aspects, inventive features, and advantages of the invention, as defined solely by the claims, are described in the non-limiting detailed description set forth below.

DETAILED DESCRIPTION OF THE EMBODIMENTS

The present application describes a system and method for laminography inspection that is cost efficient, and can effectively generate a cross-sectional image of a selected section plane within a test object using a convenient warp compensation mode of computation.

In the description hereafter, "irradiation source" means an energetic source configured to emit electromagnetic radiations used for radiography, including, but not limited to, X-ray sources, gamma sources, or the like. Further, "image detector" means a device configured to produce image signals of a test object as it receives radiations traveling from the irradiation source through the test object, including, but not limited to, X-ray detectors, gamma detectors, or the like.

Figure 1A:
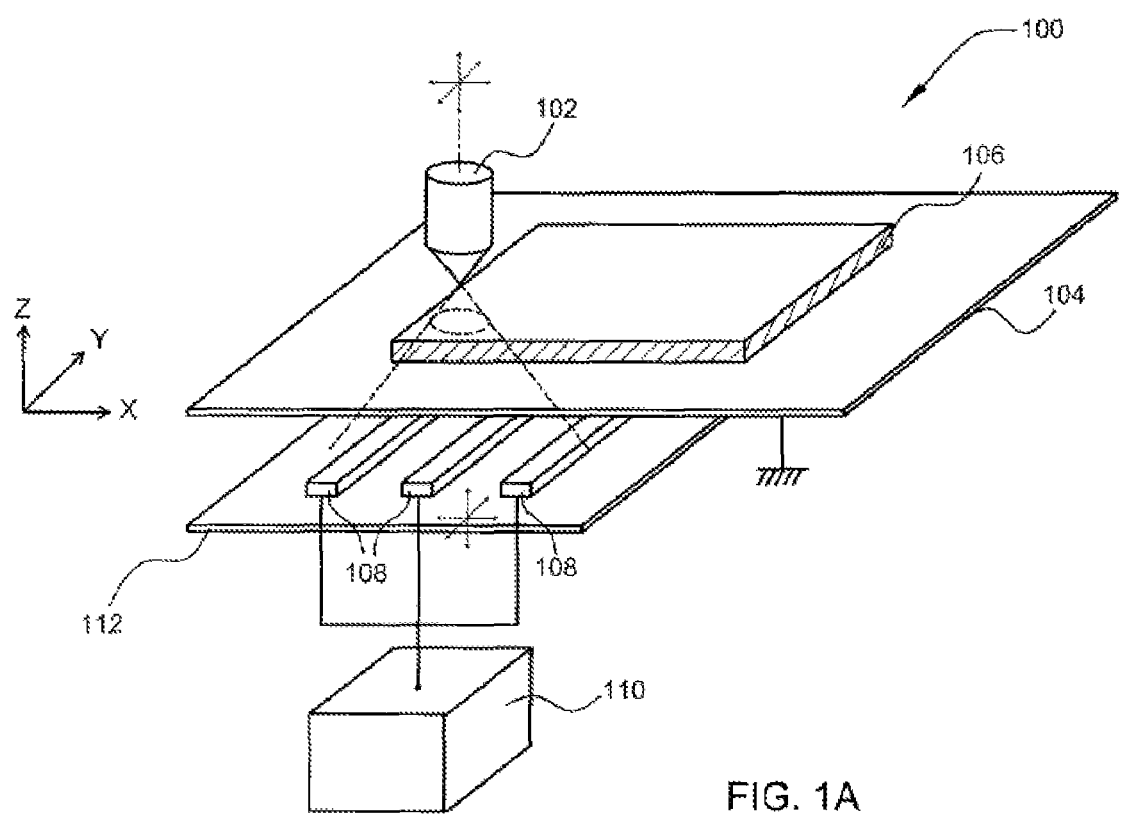
FIG. 1A is a schematic perspective view of a laminography inspection system according to one embodiment of the invention.
Figure 1B:
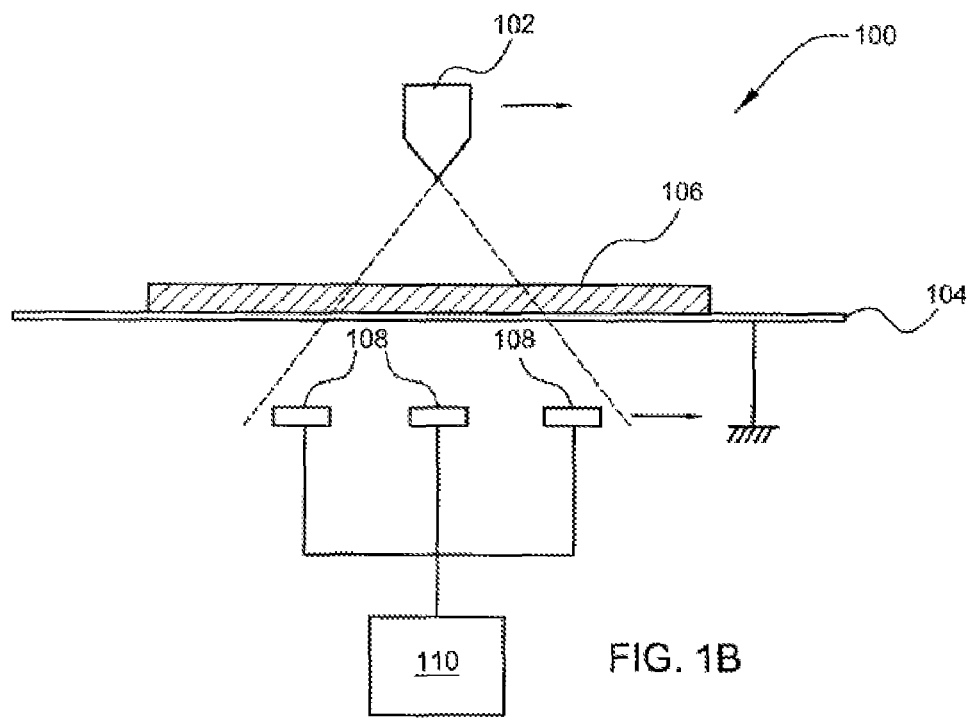
FIG. 1B is a schematic side view of a laminography inspection system according to one embodiment of the invention.

FIGS. 1A and 1B are schematic views illustrating a laminography inspection system according to one embodiment of the present invention. Inspection system 100 includes an X-ray source 102, a fixed table 104 for placement of an object 106 under examination, linear X-ray detectors 108, and a computing device 110. The X-ray source 102 is positioned above the fixed table 104 and may irradiate a conical beam of X-rays that travels through the object 106 and impinges on the detectors 108 lying underneath the object 106 opposite to the X-ray source 102. Each of the linear detectors 108 converts a pattern of X-rays that passed through the object 106 into image signals that are transmitted to the computing device 110 for analysis.

Referring to FIG. 1A, for the purpose of clearer description, an arbitrary coordinate reference (X, Y, Z) will be used hereafter to explain the mechanism of the inspection system 100. The fixed table 104 is stationary in a horizontal plane parallel to the axes X and Y. The X-ray source 102 is mounted on a vertical axle parallel to axis Z and perpendicular to the plane of the fixed table 104. The X-ray source 102 is independently driven along the axes X, Y and Z by a motor drive mechanism (not shown). The X-ray source 102 may include, but is not limited to, any standard industrial X-ray tubes.

The linear X-ray detectors 108 are placed coplanar on a support frame 112 at fixed spaced intervals along the axis X, and lie parallel to the axis Y. In one embodiment, a number of 3 linear detectors 108 may be provided, each of which is formed from linear or one-dimensional arrays of discrete X-ray sensitive elements similar to charge coupled devices. However, it will be understood that the number of linear detectors 108 may vary according to the design requirements. The support frame 112 can be independently driven along the axes X, Y and Z so as to desirably set the position of the detectors 108 relative to the test object 106 and X-ray source 102. The relative positions of the X-ray source 102 and the linear detectors 108 may be adjusted in order to set a desired focal plane and optimal resolution for the acquisition of X-ray images.

Figure 1C:
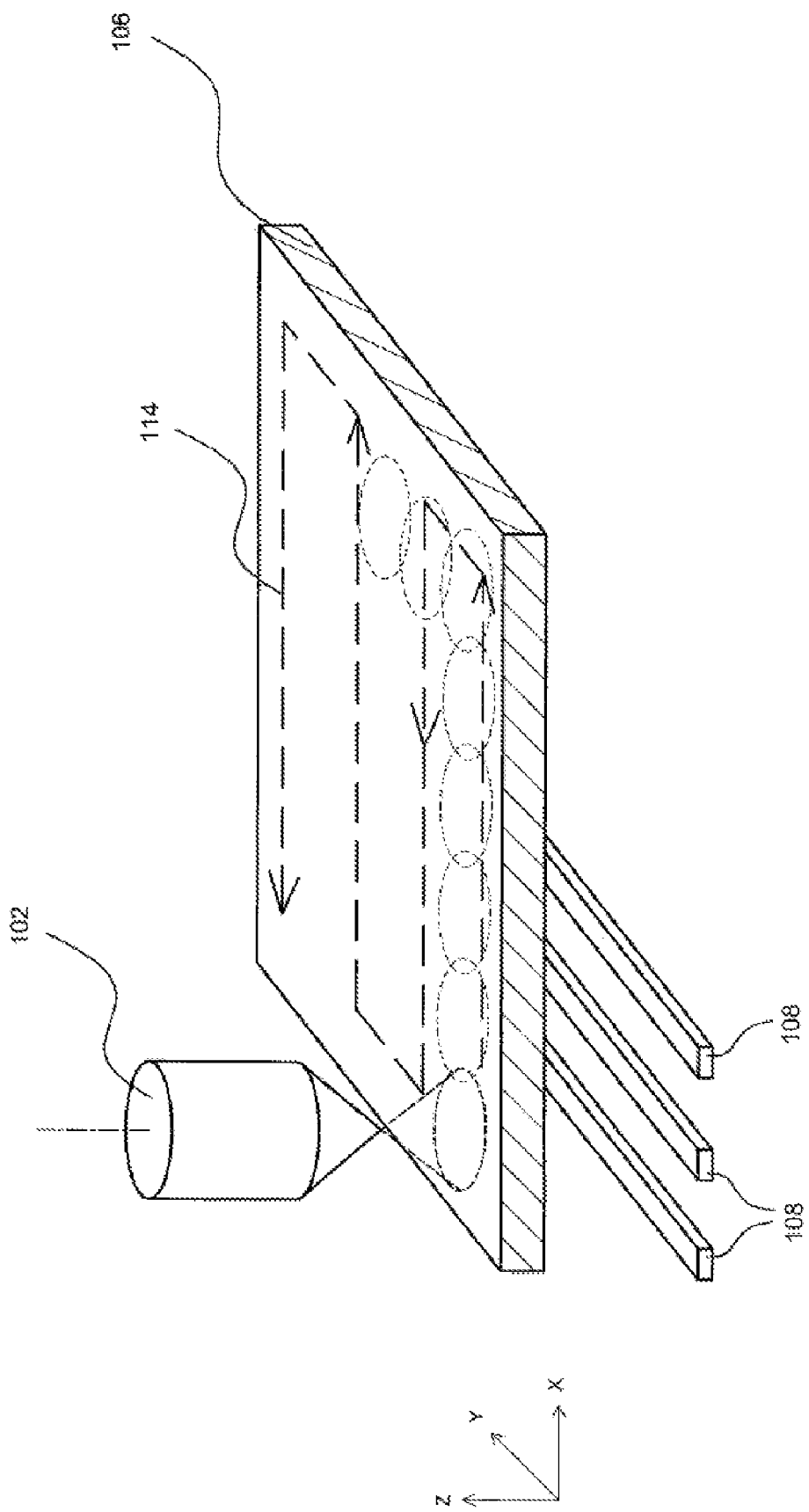
FIG. 1C is a schematic diagram illustrating a scanning operation performed within a laminography inspection system according to one embodiment of the invention.

FIG. 1C describes a preferred scanning cycle performed by the inspection system 100 according to one embodiment. In one scanning cycle, the test object 106 is stationary while the X-ray source 102 synchronously moves with the detectors 106 to scan the test object 106. The scanning cycle includes linear scanning passes 114 that are parallel to the axis X and sequentially increment with respect to the axis Y to span across the area of the test object 106. Along one pass of the scanning cycle, X-ray image data of a scanned portion of the test object 106 are respectively obtained from the 3 linear detectors 108 under 3 different viewing angles corresponding to the X-ray source 102. In one embodiment, the Y-increment between successive passes may be set so that the adjacent scanning passes will overlap. For a given scanned portion of the test object 106, the number of viewing angles can be increased by the number of scanning passes covering the scanned portion. As a result, more X-ray image data of different viewing angles may be acquired for analysis by the computing device 110 without adding any image detectors or costly scanning motions.

It will be understood that the increment between two successive passes may also be set differently, and the overlap described above is not mandatory. In addition, instead of three detectors, a different embodiment may use one single detector to perform 3 linear scanning passes under different viewing angles relative to the X-ray source 102 to acquire the same images under 3 viewing angles. Based on the acquired images, the computing device 110 is configured to generate laminographic images for inspection of the test object 106.

FIGS. 2A through 2D are schematic diagrams illustrating the geometric principles for reconstructing an X-ray image of a section P within the test object based on a combination of X-ray image data acquired under different viewing angles. For a clearer description, the following annotation will be used. Distance $H_1$ separates the X-ray source S from the image plane D where are positioned the detectors $D_1$, $D_2$ and $D_3$. Detector $D_1$ is arranged at a left angled position relative to source S, detector $D_2$ is arranged at a vertical position opposite to the source S, and detector $D_3$ is arranged at a right angled position relative to source S. Distance $H_0$ denotes the distance between the focal plane F and the X-ray source S. Distance h denotes the distance between an object section of interest P and the focal plane F. Distance $R_x$ separates two adjacent detectors, while length $R_y$ corresponds to a Y-increment between two successive scanning passes.

As a test object 106 undergoes scanning through the inspection system 100, a section within the test object 106 that is outside the focal plane F will form different images that are distorted and shifted from one another in the image plane D. As a result, in the image plane D, only images of points in the focal plane F will appear sharp while points outside the focal plane F will appear blurred. To reconstruct an image of a desired section P within the test object, the X-ray image data acquired under different viewing angles are combined with adequate shift and scale factors so that they properly overlap to generate a suitable image of the section of interest P. These shift and scale factors may be determined relative to the axes X and Y as detailed below.

Figure 2A:
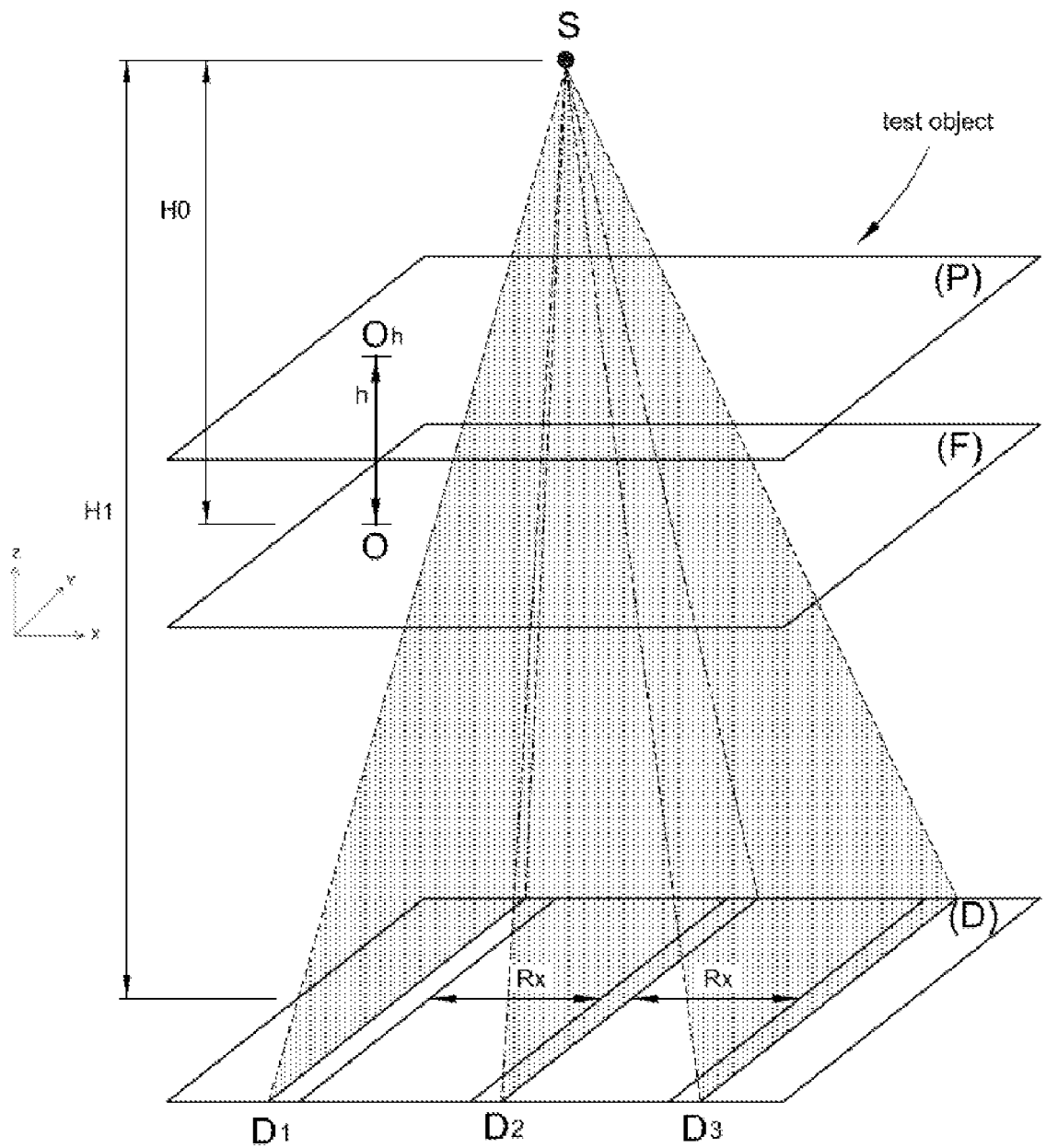
FIGS. 2A through 2D are schematic views showing the principles for reconstructing an X-ray image of a section within a test object according to the present invention.
Figure 2B:
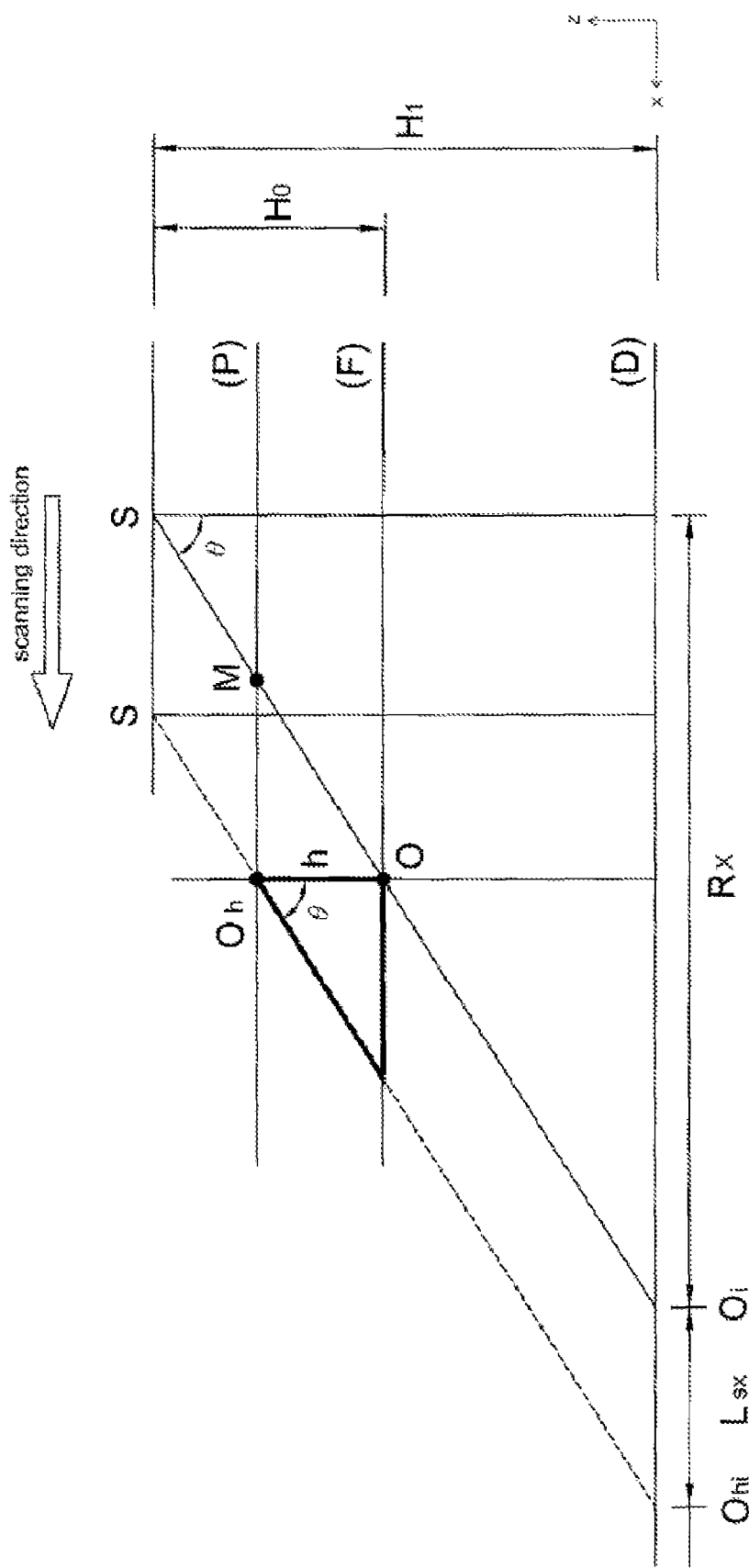

FIG. 2B illustrates the determination of the scale and shift factors in the direction X based on a projection plane parallel to the axes X and Z. From a viewpoint in this projection plane, one point O in the focal plane F will correspond to an image point $O_i$ in the image plane D, and a point $O_h$ in the section of interest P vertically above point O will correspond to the image point $O_{hi}$ in the image plane D. Based on simple geometric ray projections, the shift factor $L_{sx}$ separating $O_i$ and $O_{hi}$ in the image plane D can be derived as:

$$L_{sx} = h \times \tan \theta = h \, R_x / H_1$$

Moreover, as the X-ray source S scans linearly in the direction X, a segment $O_h M$ in the direction X within a section plane P of the test object 106 will project into the image plane D without distortion. The scale factor in the direction X thus is equal to 1.

Figure 2C:
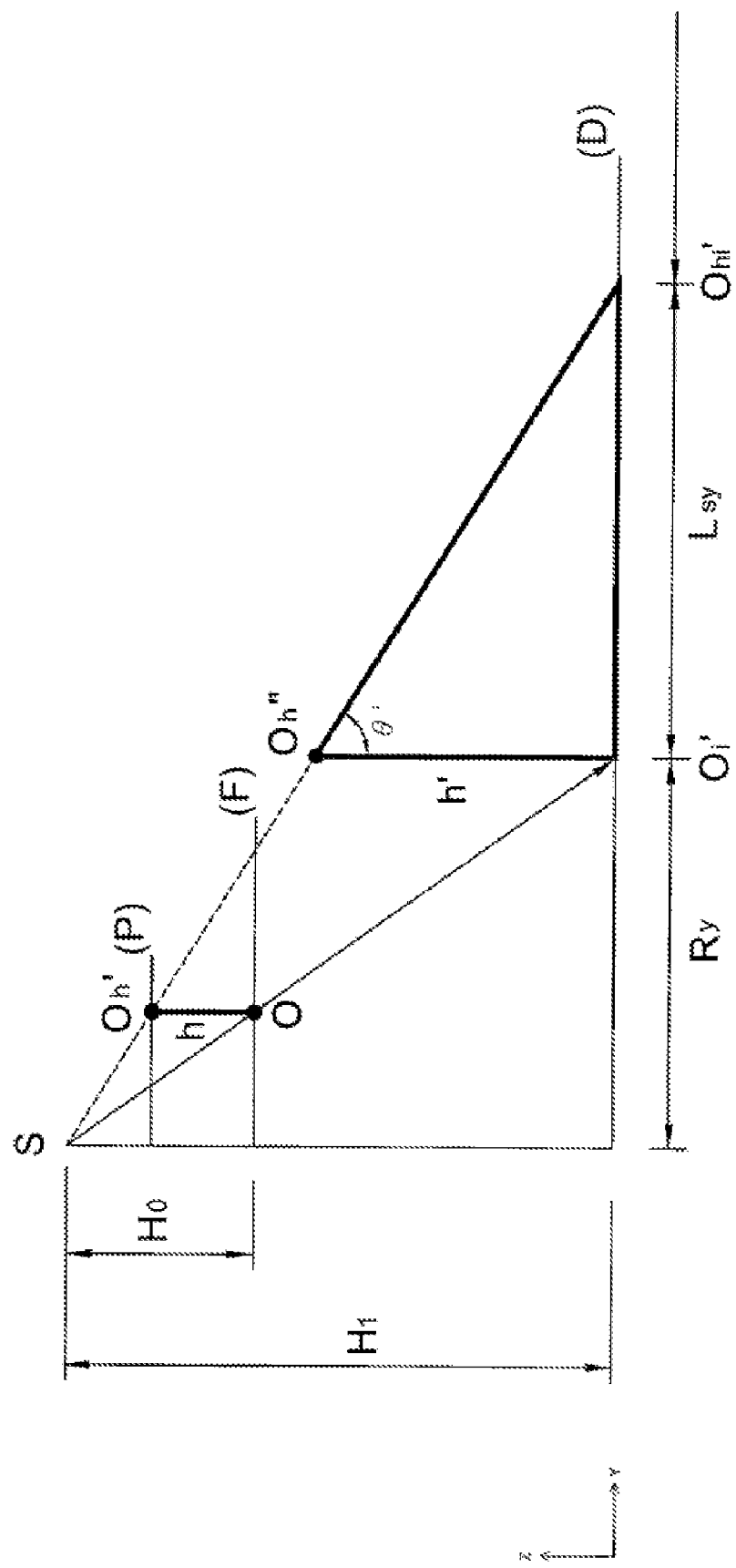

Similarly, FIG. 2C illustrates the determination of a shift factor $L_{sy}$ in the direction Y based on a projection plane parallel to the axes Y and Z. From a viewpoint in this projection plane, point O in the focal plane F will form an image point $O_i'$ in the image plane D, and point $O_h'$ in the object section of interest P vertically above point O will form the image point $O_{hi}'$ in the image plane D. The shift factor $L_{sy}$ separating $O_i'$ from $O_{hi}'$ in the image plane D can be determined with the following relationship:

$$L_{sy} = h' \times \tan \theta'$$

As $h' = h \times H_1/H_0$ and $\tan \theta' = (R_y + L_{sy})/H_1$, the shift factor $L_{sy}$ can be derived as:

$$L_{sy} = h \times R_y / (H_0 - h)$$

Figure 2D:
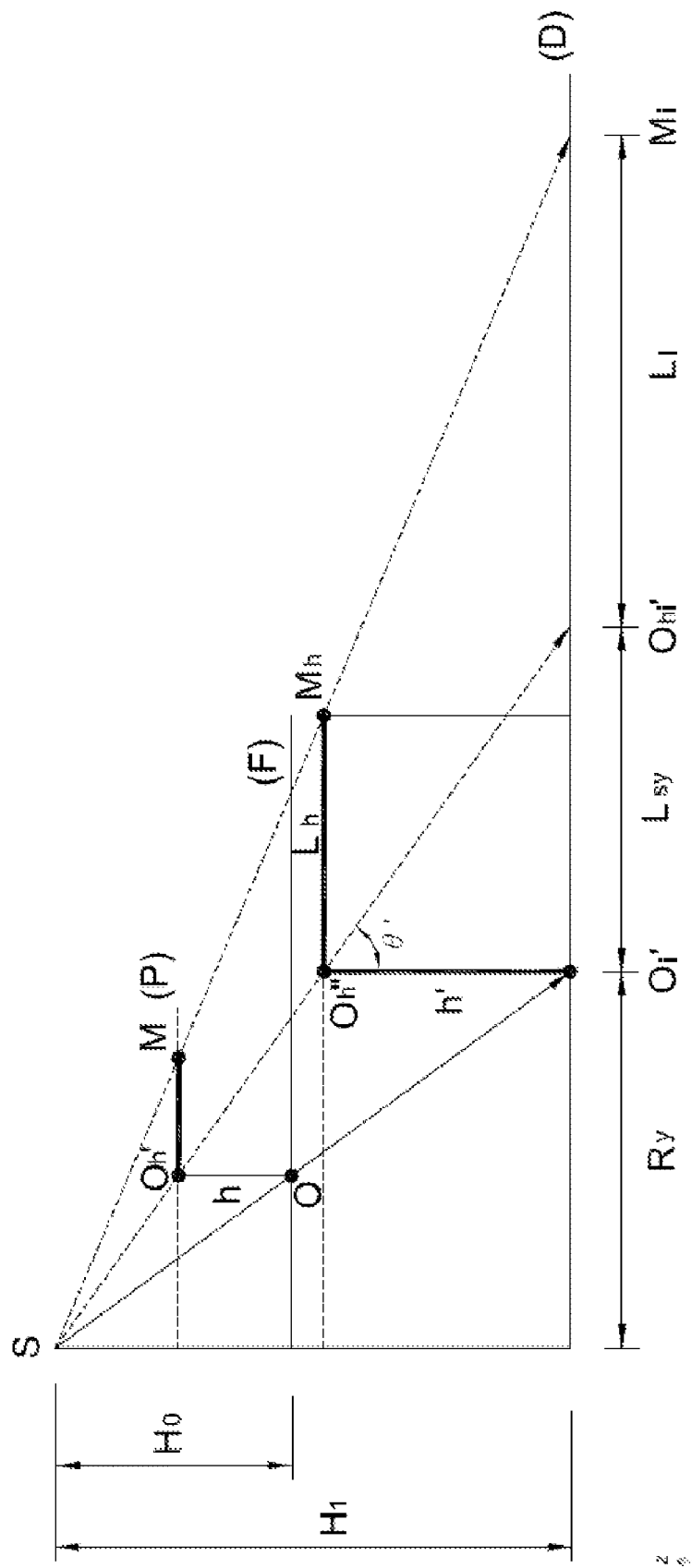

FIG. 2D illustrates the determination of a scale factor f in the direction Y made in a projected plane parallel to the axes Y and Z. Assume that a segment $O_h' M$ in the object section of interest P forms a distorted segment image $O_{hi}' M_i$ in the image plane D, the scale factor f can be defined as the ratio $O_h'' M_h / O_{hi}' M_i = L_h / L_i$. Based on the rules of similar triangles, the scale factor f in the direction Y can be derived as:

$$f = (H_1 - h')/H_1 = 1 - h/H_0$$

The following Table 1 describes the different shift and scale factors in the direction X and Y computed for reconstructing an X-ray image of a desired section within the test object defined by its height h relative to the focal plane.

TABLE 1

| | X | Y |
|---|---|---|
| shift factor | $L_{sx} = \dfrac{h \times R_x}{H_1}$ | $L_{sy} = \dfrac{h R_y}{H_0 - h}$ |
| scale factor | 1 | $f = \dfrac{L_h}{L_i} = 1 - \dfrac{h}{H_0}$ |

By applying the shift and scale factors, the combined X-ray images of the test object adequately overlap to form a reconstructed image of a desired section at a coordinate Z in the test object.

Figure 2E:
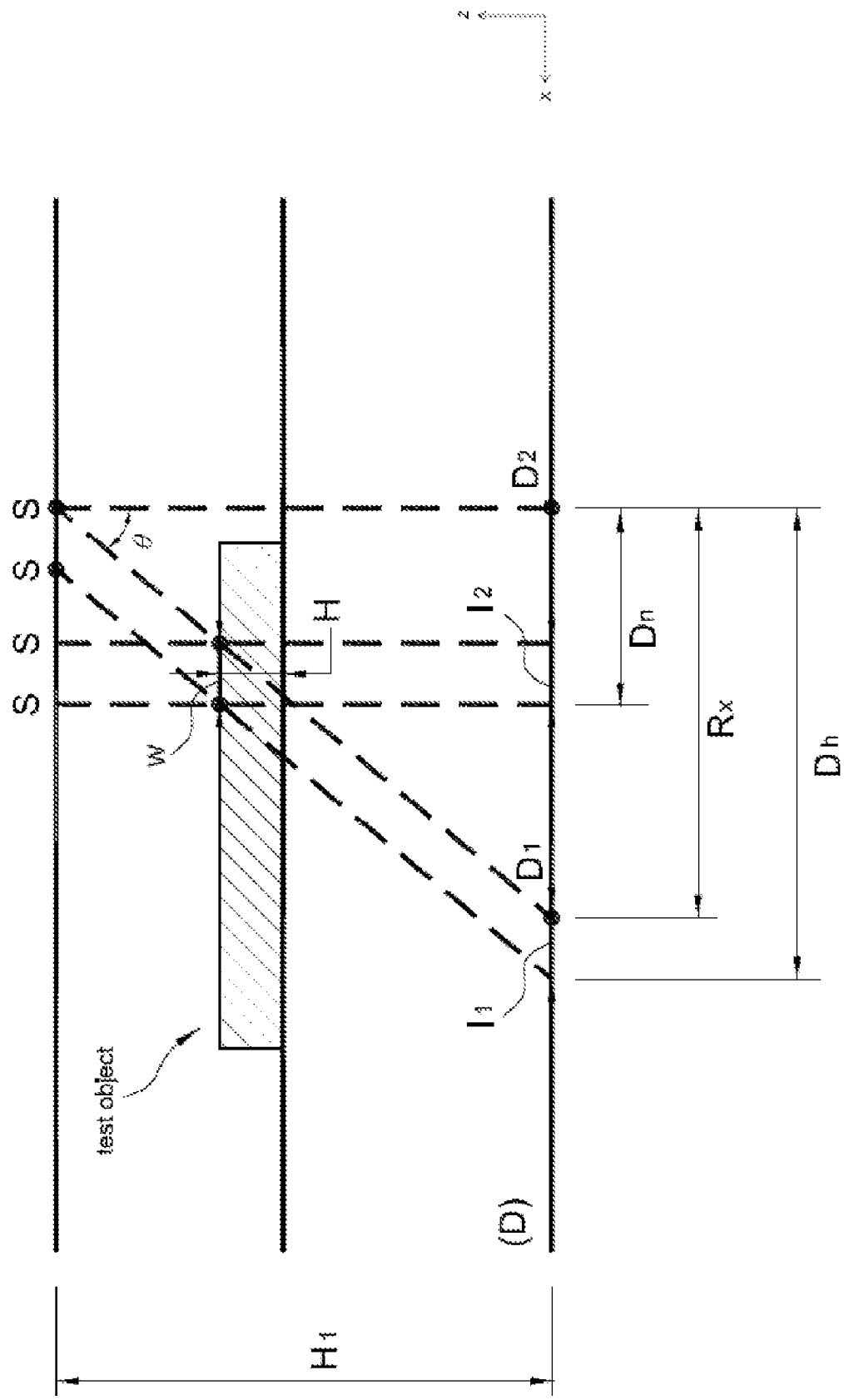
FIG. 2E illustrate the determination of a warp compensation according to the present invention.

Note that other advantages may be provided with the configuration of the X-ray inspection system according to the present invention. In particular, it may conveniently allow for a Z-axis warp compensation mode of computation. With reference to FIG. 2E, the illustrated technique for Z-axis warp compensation uses a stereo imaging method to construct a Z-map that characterizes a warp in the test object. In applying the stereo imaging method, two images $I_2$ and $I_1$ will be respectively acquired by detectors $D_2$ and $D_1$ for a feature W of the test object at a height H relative to a surface reference. Assume that $D_n$ and $D_h$ represent the respective positions of the images $I_2$ and $I_1$ and r(0) is the image resolution, the actual height H of the feature W can be derived from the following formulae:

$$H = \frac{H_1 \times (D_n - D_h) \times r(0)}{R_X}$$

By computing the above formulae over the area of the test object, a Z-map can be constructed based on the images acquired during the scanning cycle. With the constructed Z-map, the computing device can apply a warp compensation in the computed shift and scale factors so that a reconstructed laminographic image correctly reflects a selected section P of the test object, even if it is actually located at a biased position due to the occurrence of a warp in the test object. Effective warp compensation thus can be computed without the need of CAD data of the test object.

Figure 3:
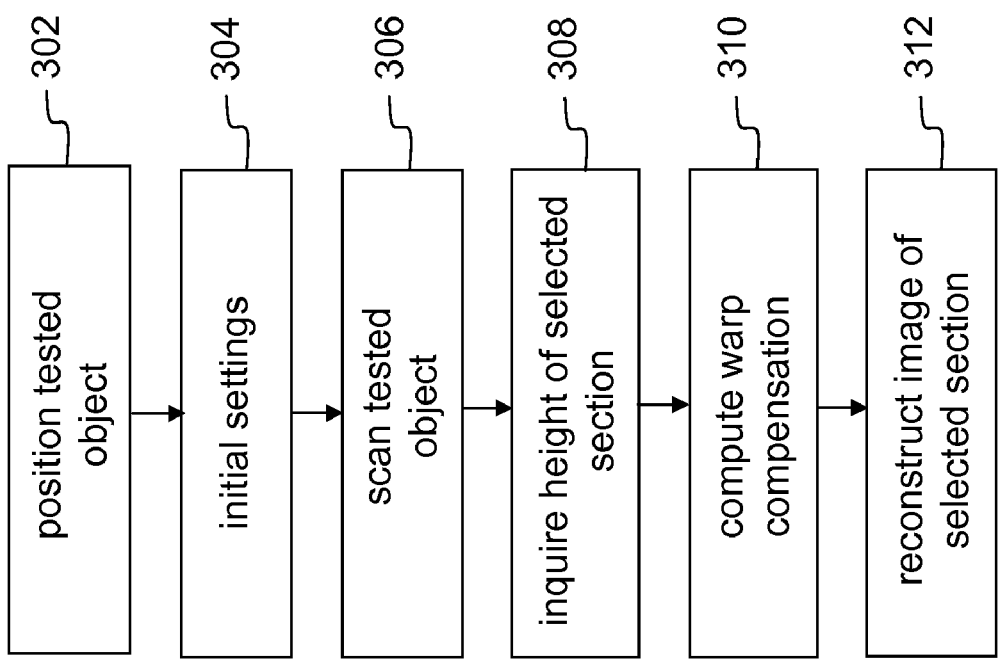
FIG. 3 is a flowchart of method steps performed within a laminography inspection system according to one embodiment of the invention.

Reference now is made to FIG. 3 in conjunction with FIGS. 1A-1C to describe the method steps for a laminography inspection according to one embodiment of the invention. In step 302, the test object 106 is placed in the inspection system 100. Before the test object is scanned for X-ray image acquisition, initial settings are made in step 304 to define the focal plane and an adequate image resolution by adjusting the relative positions between the X-ray source 102, the object 106 and the detectors 108. In step 306, a scanning operation then is performed, by which the X-ray source 102 irradiating a conical beam of X-rays synchronously moves with the detectors 106 along parallel linear scanning passes across the area of the fixed object 106. Multiple X-ray images of the test object 106 under different viewing angles are thereby acquired to reconstruct a cross-sectional image of a section of interest P within the test object 106.

For this purpose, in step 308, the inspection system 100 requests the operator to input the height h of the desired section P relative to the focal plane F. In step 310, before a cross-sectional image of the selected section P is generated, the computing device 110 may compute an object warp compensation to be applied in the reconstruction of the cross-sectional image of the selected section P. The computation of the warp compensation may be achieved by constructing a Z-map characteristic of a warp of the test object based on the acquired X-ray images, as described above in conjunction with FIG. 2E. In step 312, based on the inputted height h and the computed warp compensation, the computing device 110 calculates the proper shift and scale factors and applies these factors to combine the acquired X-ray images in order to generate a cross-sectional image of the selected section P.

Figure 4A:
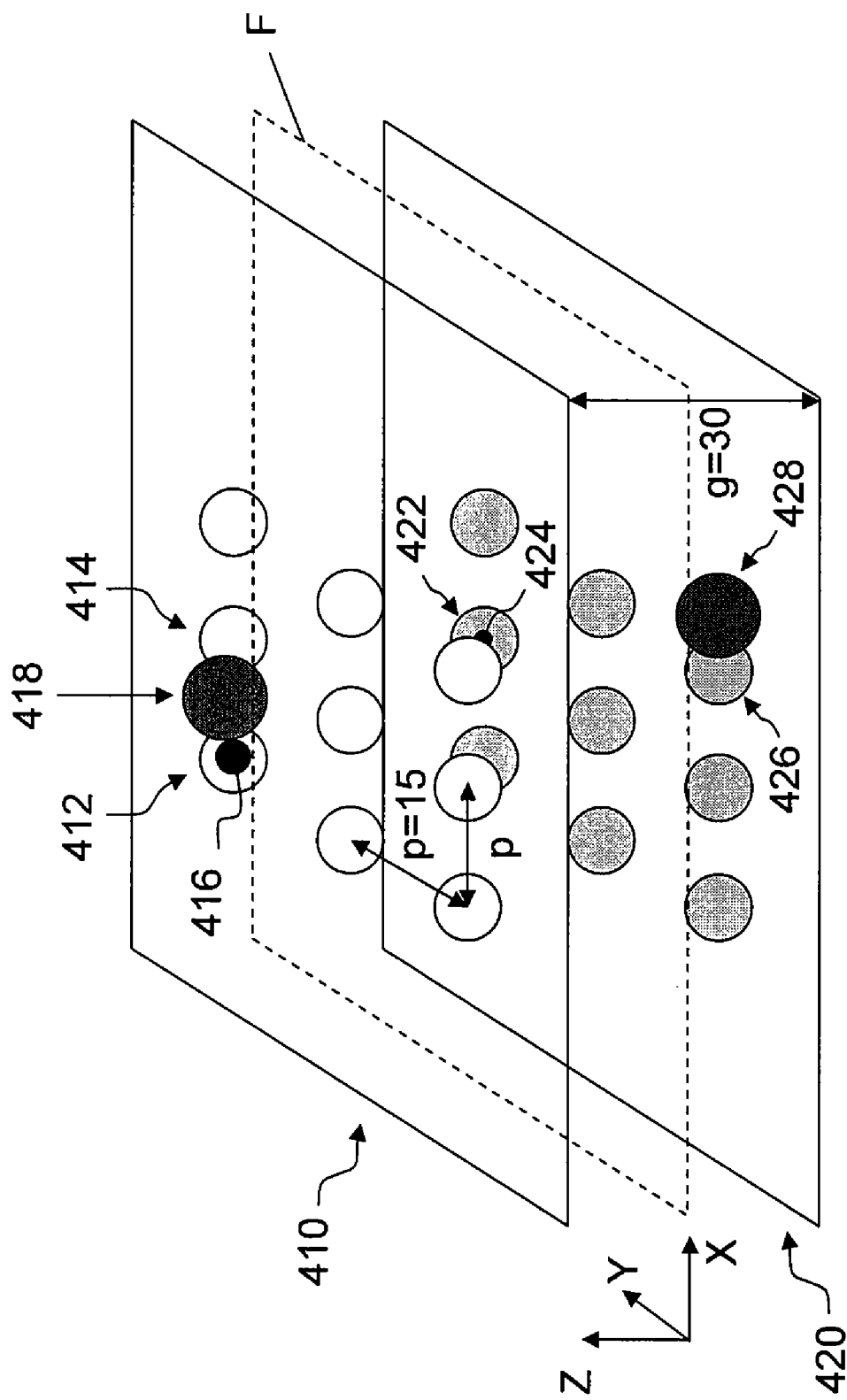
FIGS. 4A through 4E show exemplary samples of X-ray images which may be obtained with a laminography inspection method according to the present invention.

For the purpose of illustration only, FIGS. 4A through 4E show exemplary samples of images which may be obtained through a laminography inspection method according to the present invention. FIG. 4A schematically shows the configuration of the test object, which includes two layers 410 and 420 of solders respectively arranged in two parallel planes lying over each other. Each of the layers 410 and 420 includes a 3×3 array of solders. The illustrated gap "g" between the two layers 410 and 420 and inter-solder pitch "p" are expressed with arbitrary units. The focal plane F is exemplary set at the coordinate Z=0 corresponding to the middle plane equidistant from the layers 410 and 420. The test object includes a number of defects 412, 418, 424, 428 and 429 that will be apparent from the reconstructed X-ray images discussed below with reference to FIGS. 4B through 4E.

Figure 4B:
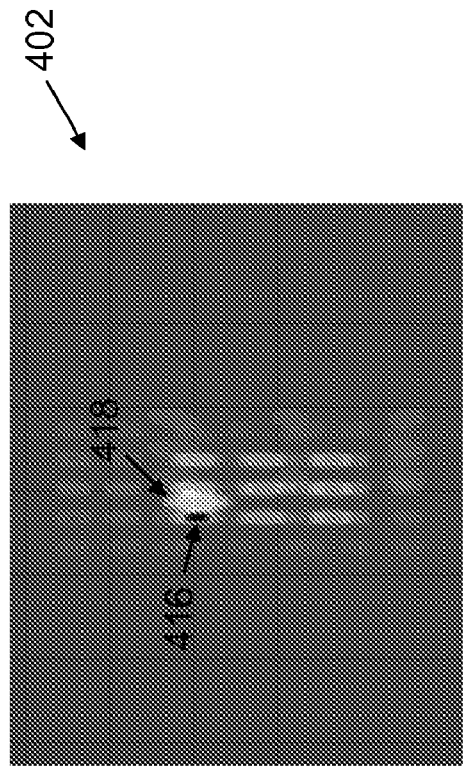
Figure 4C:
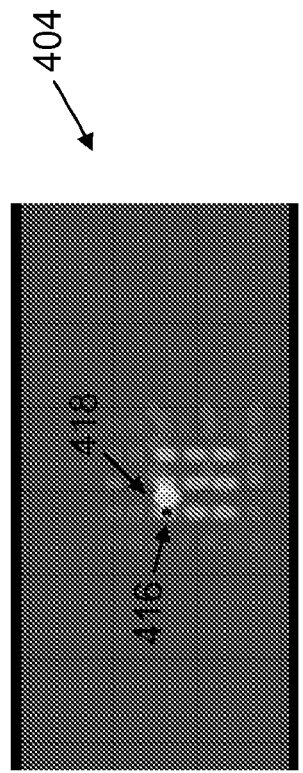

FIGS. 4B and 4C show X-ray images reconstructed for the section of the solder layer 410, which corresponds to the plane of coordinate Z=15 relative to the focal plane F. In FIG. 4B, the illustrated X-ray image 402 is obtained from a combination of acquired X-ray images that uses computed shift factors $L_{sx}$=7.5 and $L_{sy}$=35.294. As no scale factor is applied, the reconstructed X-ray image 402 appears distorted in the direction Y. FIG. 4C shows a reconstructed X-ray image 404 that is obtained from the same combination of X-ray image data plus the application of a scale factor f=0.85/2 in the direction Y, which properly corrects the scale distortion in the direction Y. Referring to FIG. 4A in conjunction with FIGS. 4B and 4C, the reconstructed X-ray images 402 and 404 correctly show the presence of a solder bridge defect 418 connecting between solders 412 and 414 and void defect 416 within the solder 412.

Figure 4D:
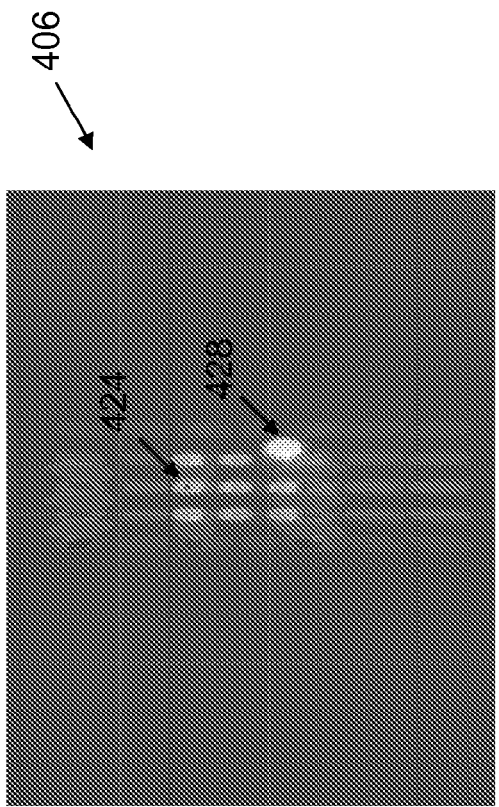
Figure 4E:
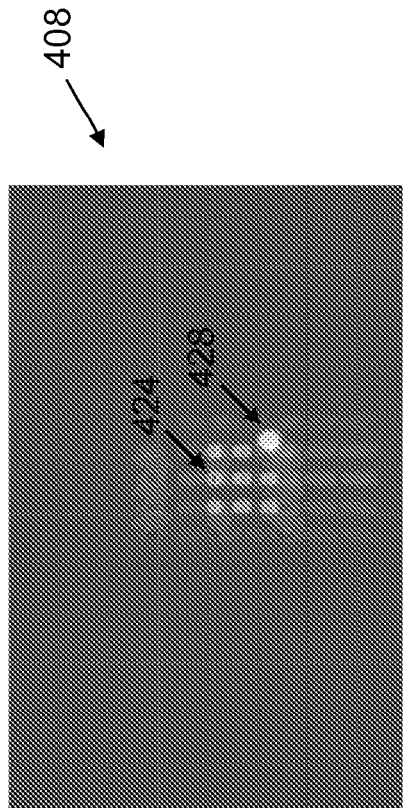

FIGS. 4D and 4E show X-ray images reconstructed for the section of the solder layer 420, which corresponds to the plane of coordinate Z=-15 relative to the focal plane F. Similarly, the illustrated X-ray image 406 of FIG. 4D is obtained from a combination of acquired X-ray images that uses computed shift factors $L_{sx}$=-7.5 and $L_{sy}$=-26.087, while X-ray image 408 of FIG. 4E is obtained from the same combination of X-ray images plus the application of a scale factor f=1.15/2 to correct the scale distortion in the direction Y. The reconstructed X-ray images 406 and 408 correctly show the presences of a solder bridge defect 428 connecting with solder 426 and void defect 424 within the solder 422.

As described above, the method and system according to the principles of the present invention can effectively reconstruct a cross-sectional image of a section of interest within the test object based on images acquired by the image detectors. The image acquisition is achieved through a cycle of parallel linear scanning passes that efficiently increases the number of viewing angles without adding image detectors.

Realizations in accordance with the present invention have been described in the context of particular embodiments. These embodiments are meant to be illustrative and not limiting the scope of present invention. Many variations, modifications, additions, and improvements are possible. Accordingly, plural instances may be provided for components described herein as a single instance. Structures and functionality presented as discrete components in the exemplary configurations may be implemented as a combined structure or component. These and other variations, modifications, additions, and improvements may fall within the scope of the invention as defined in the claims that follow.

What is claimed is:

1. A laminography inspection system comprising:
   an irradiation source;
   a plurality of linear image detectors defining an image plane;
   a site for placement of a test object in a stationary position between the irradiation source and the image detectors; and
   a computing device adapted to compute shift and scale factors and apply the shift and scale factors for combining a plurality of images of the test object acquired from the image detectors to generate a cross-sectional image of a selected section within the test object, wherein the computing device is configured to:
   process the acquired images through a stereo imaging method to determine a warp compensation of the test object, and
   apply the warp compensation in the computation of the shift and scale factors;
   wherein the irradiation source and the image detectors are configured to scan the test object through a cycle of parallel linear scanning passes spanning across the area of the test object to acquire images of the test object under different viewing angles.

2. The system of claim 1, wherein the selected section within the test object is parallel with the image plane.

3. The system of claim 1, wherein the shift and scale factors are determined relative to two coordinate axes parallel to the image plane.

4. The system of claim 3, wherein at least one scale factor relative to a coordinate axis parallel to the linear scanning passes is equal to 1.

5. The system of claim 1, wherein the shift and scale factors are determined according to a plurality of parameters including a height of the selected section in the test object relative to a focal plane, a distance between the irradiation source and the image plane, a distance between the irradiation source and the focal plane, a distance between two detectors, and an increment length between two successive scanning passes.

6. The system of claim 1, wherein the irradiation source is configured to irradiate a conical beam of X-rays that travel through the test object to impinge on the image detectors.

7. The system of claim 1, wherein the irradiation source and the image detectors are independently driven.

8. The system of claim 1, wherein the image detectors include at least one central linear detector arranged vertically opposite the irradiation source relative to the fixed table, and two side linear detectors placed at an inclined viewing angle relative to the irradiation source.

9. The system of claim 1, wherein the irradiation source irradiating a conical beam synchronously moves with the plurality of linear image detectors along parallel linear scanning passes across the area of the test object.

10. A laminography inspection method comprising:
    performing a plurality of parallel linear scanning passes across an area of a test object in a stationary position to acquire a plurality of image data of the test object under different viewing angles;
    processing the acquired image data through a stereo imaging method to determine a warp compensation of the test object;
    applying the warp compensation for computing shift and scale factors; and
    combining the image data with the shift and scale factors to reconstruct a cross-sectional image of a selected section within the test object.

11. The method of claim 10, wherein the selected section within the test object is parallel to an image plane from which the image data are acquired.

12. The method of claim 10, wherein the shift and scale factors are determined relative to two coordinate axes parallel to an image plane from which the image data are acquired.

13. The method of claim 12, wherein at least one scale factor relative to a coordinate axis parallel to the linear scanning passes is equal to 1.

14. The method of claim 10, wherein performing a plurality of parallel linear scanning passes across an area of a test object in a stationary position includes synchronously moving an irradiation source and image detectors in a cycle of parallel linear scanning passes across an area of the test object.

* * * * *